(12) United States Patent
Boebel et al.

(10) Patent No.: US 6,709,445 B2
(45) Date of Patent: Mar. 23, 2004

(54) FORCEPS FOR DISSECTING FREE TISSUE IN BODY CAVITIES

(75) Inventors: Manfred Boebel, Bauschlott (DE); Frank Knodel, Knittlingen (DE); Adolf Gallinat, Helmstorf/Seevetal (DE)

(73) Assignee: Richard Wolf GmbH, Knittlingen (DE)

( * ) Notice: Subject to any disclaimer, the term of this patent is extended or adjusted under 35 U.S.C. 154(b) by 383 days.

(21) Appl. No.: 09/789,351

(22) Filed: Feb. 21, 2001

(65) Prior Publication Data

US 2001/0021861 A1 Sep. 13, 2001

(30) Foreign Application Priority Data

Feb. 21, 2000 (DE) .......................... 100 07 919

(51) Int. Cl.[7] .......................... A61B 17/28; A61B 17/42; A61B 17/44
(52) U.S. Cl. ...................................... 606/207; 600/564
(58) Field of Search .................. 606/170, 171, 606/190, 205, 206, 207, 210, 167, 198; 600/564

(56) References Cited

U.S. PATENT DOCUMENTS

| | | | |
|---|---|---|---|
| 5,019,091 A | * 5/1991 | Porat et al. ............... 606/205 |
| 5,201,752 A | 4/1993 | Brown et al. | |
| 5,522,839 A | 6/1996 | Pilling | |
| 5,549,627 A | * 8/1996 | Kieturakis ............... 606/206 |
| 5,599,279 A | 2/1997 | Slotman et al. | |
| 5,658,307 A | 8/1997 | Exconde | |
| 5,722,988 A | * 3/1998 | Weisshaupt ............... 606/205 |
| 5,893,878 A | 4/1999 | Pierce | |
| 5,904,647 A | * 5/1999 | Ouchi ............... 600/104 |
| 5,919,205 A | * 7/1999 | Heimberger et al. ...... 606/205 |
| 5,993,461 A | 11/1999 | Abae | |
| 6,206,904 B1 | * 3/2001 | Ouchi ............... 606/207 |
| 6,391,043 B1 | * 5/2002 | Moll et al. ............... 606/174 |

FOREIGN PATENT DOCUMENTS

| | | |
|---|---|---|
| DE | 1 124 184 | 7/1960 |
| EP | 0 835 637 A1 | 4/1998 |
| WO | WO 99/30622 | 6/1999 |

\* cited by examiner

Primary Examiner—Henry Bennett
Assistant Examiner—Kathryn Odland
(74) Attorney, Agent, or Firm—Akin Gump Strauss Hauer & Feld, LLP

(57) ABSTRACT

A forceps serves in particular for excising myomas located intramurally in the uterus and including a forceps jaw having two branches which are pivotable about a common axis in a working plane for opening and closing the forceps jaw and which bear against one another with structured gripping surfaces with a closed, empty forceps jaw. The branches are each provided over a part of their length with a tooth-shaped back profile and a longitudinal cutting blade on their outer back sides lying opposite the gripping surfaces.

7 Claims, 2 Drawing Sheets

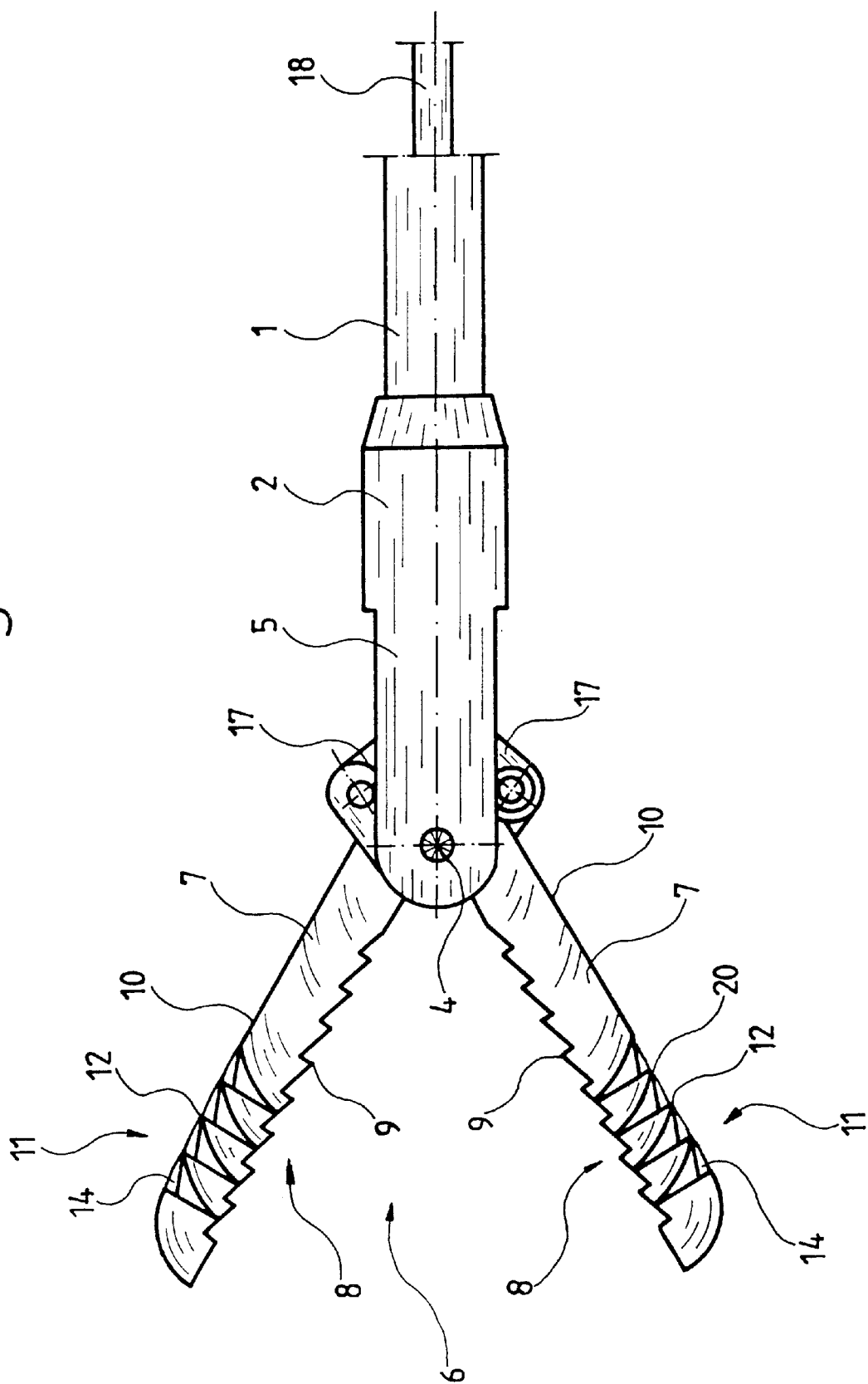

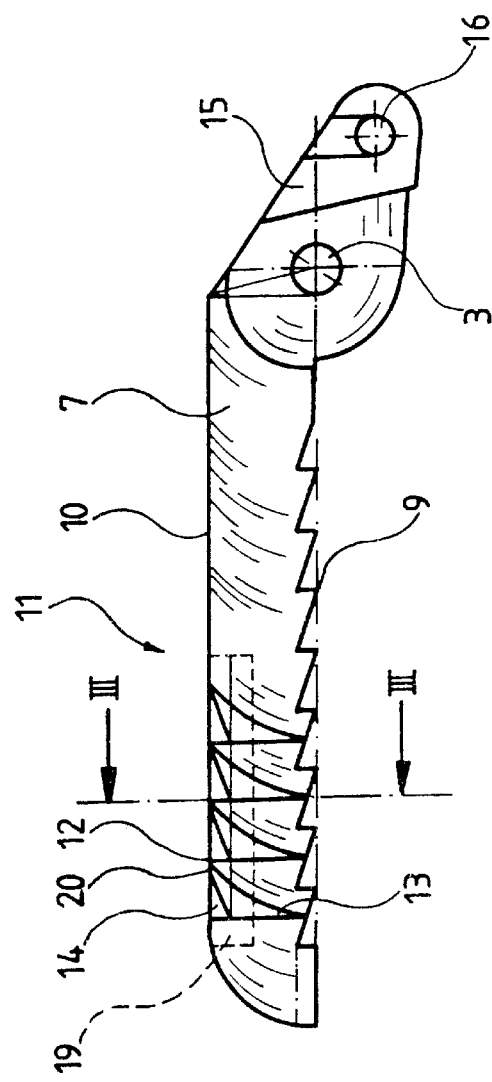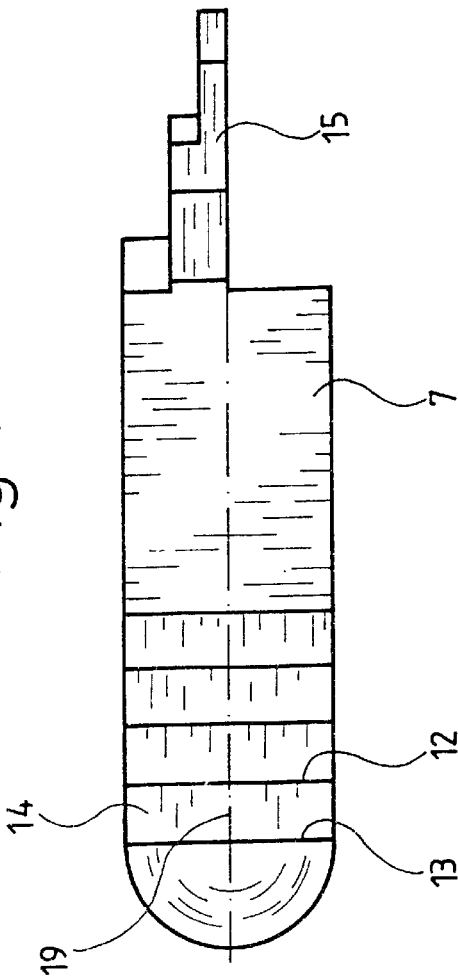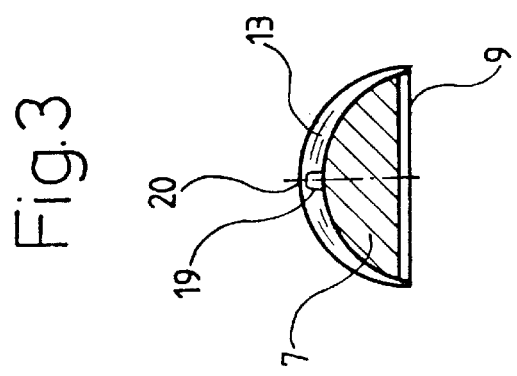

FORCEPS FOR DISSECTING FREE TISSUE IN BODY CAVITIES

BACKGROUND OF THE INVENTION

The invention proceeds from a forceps for dissecting free (i.e., excising) tissue in body cavities, in particular myomas sitting intramurally in the uterus, comprising a forceps jaw with two branches which are pivotable about a common axis in opposing directions in a working plane for opening and closing the forceps jaw and, with a closed, empty forceps jaw, bear against one another with structured gripping surfaces.

Such forceps comprise a forceps jaw with two branches which have smooth surfaces on their back sides and which are introduced into the region between the myoma and uterus wall with the forceps jaw closed, and are retracted in the spread condition, thus with an opened forceps jaw. In this manner, the tissue structures connecting the myoma to the uterus wall are severed. However, it has been shown here that already upon spreading the branches, and in particular with a pulling of the opened forceps jaw in the proximal direction, the grasped tissue slides off the back of the branches in an uncontrolled manner, and therefore is not separated. Furthermore, the branches in the known forceps are designed relatively short, so that only a small part of the tissue may be loaded, which limits the efficiency of the forceps.

BRIEF SUMMARY OF THE INVENTION

It is therefore an object of the invention to provide a forceps with which the separating effect is considerably improved and which, as a whole, may be applied more efficiently.

Proceeding from a forceps of the above mentioned type, this object is achieved according to the invention in that the branches are each provided over a part of their length with a tooth-shaped back profile on their outer back sides lying opposite the gripping surface.

The advantages which may be achieved with this lie particularly in the fact that when the forceps jaw is introduced between the myoma and the uterus wall and subsequently opened, the tissue which is thereby loaded onto the backs of the branches is prevented by the back profile from slipping from the branches. The tissue may thus be put safely under the tension required for a separation and may be perfectly severed upon retraction the opened forceps jaw. The safety of the severing of the tissue is here even further increased in that a blade with an outwardly directed cutter is arranged longitudinally in the middle of each back profile. The blade preferably terminates with the back profile in a flush manner, i.e. lies in a plane with the neighboring apexes of the back profile.

According to a further preferred feature, the back profile may be designed with a saw-tooth shape, wherein the teeth may run transversely over the back of the branches and extend up to the region of the branch gripping surfaces. A design in which each tooth has a standing flank which connects to a retrograde running flank of the respective proximally following tooth has been shown to be particularly effective within the context of the object of the invention.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings:

FIG. 1 is an overall side view of the distal-side part of the forceps according to the invention, in an opened condition;

FIG. 2 is an enlarged side view of a disassembled branch of the forceps according to FIG. 1;

FIG. 3 is a cross section through the branch according to FIG. 2 along the section line III—III; and FIG. 4 is a plan view of the branch according to FIG. 2.

DETAILED DESCRIPTION OF THE INVENTION

As can be seen from FIG. 1 the forceps according to the invention comprises a tubular shank 1, which on the proximal end is connected in a known manner to a (not shown) forceps handle with a pivotably movable grip part and on the distal end comprises a cylindrical forked head 2, which in the region of its distal end is provided with a transverse bore 3 (FIG. 2). The transverse bore serves the accommodation of an axle 4 about which the two branches, which project into the region between between the fork limbs 5 of the forked head 2 and which form a forceps jaw 6, are mounted in a pivotably movable manner.

The two branches 7 are provided with grip surfaces 8, in whose plane runs the axle 4, which are structured by a multitude of teeth 9 which bear against one another with a closed, empty forceps jaw 6. In the closed position the branches 7 form a quasi cylindrical body, which is parted in the plane of the axle 4, which continues proximally with lever arms 15 in the cylindrical forked head 2, and which is rounded in a spherical manner at its distal end. Accordingly, the distal ends of the branches 7 are shaped atraumatically, and seen in cross section the branch backs 10 are rounded (semi-circular).

The branches 7 are provided over a part of their length on their outer surface forming the back 10 with a tooth-shaped back profile 11, whose teeth 12 are designed saw-tooth-shaped and have a standing flank 13 to which there connects a retrograde running flank 14 of the respective proximally following tooth 12. The teeth 12 extend transversely over the back 10 of the branches, begin in the vicinity of the structured gripping surfaces 8, and run with an increasing height to the back apex where the teeth interstices have the greatest depth.

The opening and the closing of the forceps jaw is effected by known means and in the usual manner by axial adjustment of an actuation rod 18. On the proximal end each branch 7 ends in an angled lever arm 15 which has in the region of its respective proximal end a transverse bore 16 in which is arranged a bearing pin connected to a rod 17. On the proximal end the rod 17 is fastened, likewise via a pin-hole connection, onto the distal end of the actuation rod 18. This runs through the shank 1 and is proximally connected to a pivotably movable grip part of a handle, whose other grip part is rigidly connected on the shank 1.

Upon opening the forceps jaw, introduced between the uterus wall and the myoma, by way of suitable pressure application, there is already effected a tissue separation. If then with the opened forceps jaw the forceps is pulled proximally, the tissue located in the movement path of the branches 7 is loaded under an increasing tension onto the backs 10 of the branches, whereby the tissue reaches into the interstices between the teeth 12 and will bear on the standing flanks 13 of the teeth, which hold the tissue loaded in the region of the branches and secure the tissue from sliding off. Thus, a secure separating process is ensured, which may be still further facilitated and improved, in that longitudinally in the middle of the respective back profiles 11 of the branches 7, there is arranged a blade 19 with an outwardly directed cutter 20, which usefully however does not project beyond the back profile.

Normally, the separating procedure is to be carried out several times until finally the myoma is completely released from the uterus wall, and by grasping with the forceps jaw may be removed from the uterus. The separating of the myoma is effected endoscopically with observation, wherein the forceps is pushed as an auxiliary instrument through a working channel in the endoscope with its forceps jaw up to the location of operation. After cutting up the myoma, its pieces may be removed via the cervical canal. With small myomas these may also be grasped with the forceps and be removed from the body cavity together with the endoscope.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A forceps for excising tissue in body cavities, in particular myomas located intramurally in a uterus, comprising a forceps jaw having two branches which are pivotable about a common axis in opposing direction in a working plane for opening and closing the forceps jaw, the forceps jaw having structured gripping surfaces which bear against one another with a closed, empty forceps jaw, wherein the branches are each provided over a part of their length with a tooth-shaped back profile on an outer side of their backs lying opposite the gripping surfaces, and wherein a blade with an outwardly directed cutter is arranged longitudinally in a middle of each back profile.

2. The forceps according to claim 1, wherein the cutter terminates with the back profile in a flush manner.

3. The forceps according to claim 1, wherein the back profile has a saw-tooth shape, and wherein the teeth run transversely over the backs of the branches.

4. The forceps according to claim 3, wherein the teeth extend to a region of the branch gripping surfaces.

5. The forceps according to claim 3, wherein the teeth each have a standing flank which connects to a retrograde running flank of an adjacent proximally following tooth.

6. The forceps according to claim 1, wherein the cutter is substantially rectilinear in the longitudinal direction.

7. The forceps according to claim 3, wherein the teeth have substantially curvilinear edges in the transverse direction.

\* \* \* \* \*